United States Patent [19]
Maubru

[11] Patent Number: 6,099,590
[45] Date of Patent: Aug. 8, 2000

[54] OXIDATION DYEING COMPOSITION FOR KERATIN FIBERS CONTAINING CHOLINE OXIDASE

[75] Inventor: Mireille Maubru, Chatou, France

[73] Assignee: L'Oreal, Paris, France

[21] Appl. No.: 09/308,579

[22] PCT Filed: Aug. 11, 1998

[86] PCT No.: PCT/FR98/01796

§ 371 Date: May 21, 1999

§ 102(e) Date: May 21, 1999

[87] PCT Pub. No.: WO99/15140

PCT Pub. Date: Apr. 1, 1999

[30] Foreign Application Priority Data

Sep. 23, 1997 [FR] France .................................. 97 11823

[51] Int. Cl.$^7$ ...................................................... A61K 7/13
[52] U.S. Cl. ........................... 8/401; 8/406; 8/407; 8/408; 8/409; 8/410; 8/411; 8/412
[58] Field of Search ................................ 8/401, 406, 407, 8/408, 409, 410, 411, 412

[56] References Cited

U.S. PATENT DOCUMENTS

| | | | |
|---|---|---|---|
| 3,907,799 | 9/1975 | O'Brien | 544/281 |
| 4,961,925 | 10/1990 | Tsujino et al. | 424/70.2 |

FOREIGN PATENT DOCUMENTS

| | | |
|---|---|---|
| 0 310 675 | 4/1989 | European Pat. Off. . |
| 0 628 559 | 12/1994 | European Pat. Off. . |
| 0 716 846 | 6/1996 | European Pat. Off. . |
| 0 795 313 | 9/1997 | European Pat. Off. . |
| 2 112 549 | 6/1972 | France . |
| 2 586 913 | 3/1987 | France . |
| 2 733 729 | 11/1996 | France . |
| 2 359 399 | 6/1975 | Germany . |
| 3 843 892 | 6/1990 | Germany . |
| 4 133 957 | 4/1993 | Germany . |
| 195 43 988 | 5/1997 | Germany . |
| 88-169571 | 7/1988 | Japan . |
| 91-33495 | 2/1991 | Japan . |
| 0 745 144 | 2/1956 | United Kingdom . |
| 1 026 978 | 4/1966 | United Kingdom . |
| 1 153 196 | 5/1969 | United Kingdom . |
| WO 94/08969 | 4/1994 | WIPO . |
| WO 94/08970 | 4/1994 | WIPO . |
| WO 95/01426 | 1/1995 | WIPO . |
| WO 96/15765 | 5/1996 | WIPO . |
| WO 97/23685 | 7/1997 | WIPO . |

OTHER PUBLICATIONS

Erimitas Alcade et al., Etude de la réaction du β–aminocrotonitrile et dy α–formyl phénylacétonitrile avec l'hydrazine: synthése d'amino–7 pyrazolo[1,5–α]pyrimidines, Journal of Heterocyclic Chemistry, vol. 11, No. 3, Jun. 1974, pp. 423–429.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine With α–Aminocrotononitrile: Synthesis of 2,7–Dimethyl–5–Aminopyrazolo[1,5–α]Pyrimidine", Heterocycles, vol. 6, Nos. 9, 10, 1977, pp. 1355–1360.

Thomas Novinson et al., "Synthesis and Antifungal Properties of Certain 7–Alkylaminopyrazolo[1,5–α]pyrimidines", Journal of Medicinal Chemistry, vol. 20, No. 23, 1977, pp. 296–299.

Vishnu J. Ram et al., "Synthesis of bioisosteric pyrazolo[1,5–α]pyrimidines as leishmanicides", Indian Journal of Chemistry, vol. 34B, Jun. 1995, pp. 514–520.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

Robert H. Springer et al., "Synthesis and Enzymic Activity of 6–Carbethoxy– and 6–Ethoxy–3,7–disubstituted–pyrazolo[1,5–α]pyrimidines and Related Derivatives as Adenosine Cyclic 3', 5'–Phosphate Phosphodiesterase Inhibitors", Journal of Medicinal Chemistry, vol. 25, No. 8, Mar. 1982, pp. 235–242.

English Language Derwent Abstract of DE 2 359 399, Jun. 1975.

English Language Derwent Abstract of DE 3 843 892, Jun. 1990.

English Language Derwent Abstract of DE 4 133 957, Apr. 1993.

English Language Derwent Abstract of DE 195 43 988, May 1997.

English Language Derwent Abstract of EP 0 795 313, Sep. 1997.

English Language Derwent Abstract of FR 2 586 913, Mar. 1987.

English Language Derwent Abstract of FR 2 733 749, Nov. 1996.

English Language Derwent Abstract of JP 91–33495, Feb. 1991.

English Language Derwent Abstract of JP 2019576, Jan. 1990.

*Primary Examiner*—Caroline D. Liott
*Attorney, Agent, or Firm*—Finnegan, Henderson, Farabow, Garrett & Dunner, L.L.P.

[57] ABSTRACT

The invention relates to a ready-to-use composition for the oxidation dyeing of keratin fibres, and in particular of human keratin fibres such as the hair, this composition comprising, in a medium which is suitable for dyeing, at least one oxidation base, choline oxidase, and at least one donor for the said choline oxidase, as well as to the dyeing process using this composition.

49 Claims, No Drawings

OXIDATION DYEING COMPOSITION FOR KERATIN FIBERS CONTAINING CHOLINE OXIDASE

The invention relates to a composition for the oxidation dyeing of keratin fibres, and in particular of human keratin fibres such as the hair, this composition comprising, in a medium which is suitable for dyeing, at least one oxidation base, choline oxidase, and at least one donor for the said choline oxidase, as well as to the dyeing process using this composition.

It is known to dye keratin fibres, and in particular human hair, with dye compositions containing oxidation dye precursors, in particular ortho- or para-phenylenediamines, ortho- or para-aminophenols and heterocyclic bases which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of compounds used as regards the oxidation bases and the couplers allows a wide range of colours to be obtained.

The so-called "permanent" coloration obtained by means of these oxidation dyes must moreover satisfy a certain number of requirements. Thus it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide has the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation dye precursor of benzenic type in combination with enzymes such as pyranose oxidase, glucose oxidase or uricase, in the presence of a donor for the said enzymes. Although being used under conditions which do not result in degradation of the keratin fibres which is comparable to that caused by the dyes used in the presence of hydrogen peroxide, these dyeing processes are not entirely satisfactory, in particular as regards the strength of the colorations obtained.

Now, the Applicant has just discovered that it is possible to obtain novel dyes, capable of leading to colorations that are stronger than those of the prior art using an enzymatic system, by combining at least one oxidation base, at least one enzyme of choline oxidase type, and at least one donor for the said enzyme.

This discovery forms the basis of the present invention.

A first subject of the invention is thus a ready-to-use composition for the oxidation dyeing of keratin fibres, and in particular of human keratin fibres such as the hair, characterized in that it comprises, in a medium which is suitable for dyeing:

at least one oxidation base,
choline oxidase,
and at least one donor for the said choline oxidase.

The dye composition in accordance with the invention makes it possible to obtain colorations that are stronger than those obtained with the compositions of the prior art using an enzymatic oxidizing system, such as, for example, the uric acid/uricase oxidizing system.

Furthermore, the colorations obtained with the dye composition in accordance with the invention are relatively unselective and show good resistance to the various attacking factors to which the hair may be subjected (light, bad weather, washing, permanent-waving, etc.).

A subject of the invention is also a process for the oxidation dyeing of keratin fibres using this ready-to-use dye composition.

The nature of the oxidation base(s) used in the ready-to-use dye composition is not a critical factor. They can be chosen, in particular, from para-phenylenediamines, double bases, para-aminophenols, ortho-aminophenols and heterocyclic oxidation bases.

Among the para-phenylenediamines which can be used as oxidation bases in the dye compositions in accordance with the invention, mention may be made in particular of the compounds of formula (I) below, and the addition salts thereof with an acid:

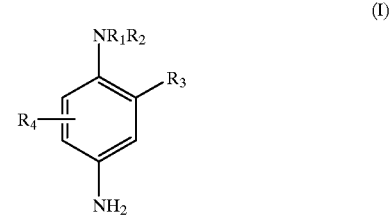

(I)

in which:
R$_1$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ alkyl radical substituted with a nitrogenous group, a phenyl radical or a 4'-aminophenyl radical;

R$_2$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous group;

R$_3$ represents a hydrogen atom, a halogen atom such as a chlorine, bromine, iodine or fluorine atom, a C$_1$–C$_4$ alkyl radical, a C$_1$–C$_4$ monohydroxyalkyl radical, a C$_1$–C$_4$ hydroxyalkoxy radical, an acetylamino(C$_1$–C$_4$)

alkoxy radical, a $C_1-C_4$ mesylaminoalkoxy radical or a carbamoylamino($C_1-C_4$)alkoxy radical, $R_4$ represents a hydrogen or halogen atom or a $C_1-C_4$ alkyl radical.

Among the nitrogenous groups of formula (I) above, mention may be made in particular of amino, mono($C_1-C_4$) alkylamino, di($C_1-C_4$)alkylamino, tri($C_1-C_4$)alkylamino, monohydroxy($C_1-C_4$)alkylamino, imidazolinium and ammonium radicals.

Among the para-phenylenediamines of formula (I) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

According to the invention, the term "double bases" is understood to refer to the compounds containing at least two aromatic rings bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

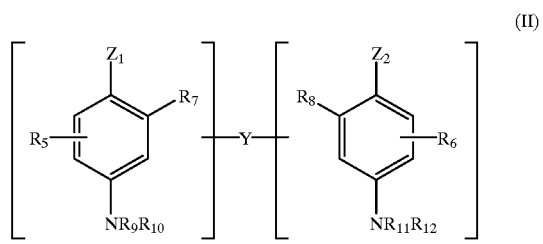

in which:

$Z_1$ and $Z_2$, which may be identical or different, represent a hydroxyl or —$NH_2$ radical which may be substituted with a $C_1-C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1-C_6$ alkoxy radicals;

$R_5$ and $R_6$ represent a hydrogen or halogen atom, a $C_1-C_4$ alkyl radical, a $C_1-C_4$ monohydroxyalkyl radical, a $C_2-C_4$ polyhydroxyalkyl radical, a $C_1-C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1-C_4$ alkyl radical;

it being understood that the compounds of formula (II) contain only one linker arm Y per molecule.

Among the nitrogenous groups of formula (II) above, mention may be made in particular of amino, mono($C_1-C_4$) alkylamino, di($C_1-C_4$)alkylamino, tri($C_1-C_4$)alkylamino, monohydroxy($C_1-C_4$)alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds corresponding to formula (III) below, and the addition salts thereof with an acid:

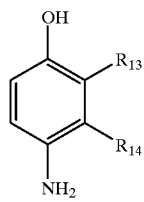

(III)

in which:
R$_{13}$ represents a hydrogen or halogen atom or a C$_1$–C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy(C$_1$–C$_4$) alkylamino(C$_1$–C$_4$)alkyl radical, R$_{14}$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl radical, it being understood that at least one of the radicals R$_{13}$ or R$_{14}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-333,495, or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo[1,5-a]pyrimidines of formula (IV) below, and the addition salts thereof with an acid or with a base and the tautomeric forms thereof, when a tautomeric equilibrium exists:

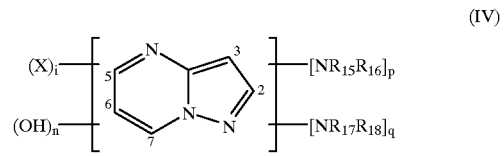

(IV)

in which:
R$_{15}$, R$_{16}$, R$_{17}$ and R$_{18}$, which may be identical or different, denote a hydrogen atom, a C$_1$–C$_4$ alkyl radical, an aryl radial, a C$_1$–C$_4$ hydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ aminoalkyl radical (it being possible for the amine to be protected with an acetyl, ureido or sulphonyl radical), a (C$_1$–C$_4$)alkylamino(C$_1$–C$_4$)alkyl radical, a di[(C$_1$–C$_4$)alkyl]amino(C$_1$–C$_4$)alkyl radical (it being possible for the dialkyl radicals to form a 5- or 6-membered carbon-based ring or heterocycle), a hydroxy(C$_1$–C$_4$)alkyl- or di[hydroxy(C$_1$–C$_4$)alkyl] amino(C$_1$–C$_4$)alkyl radical;

the radicals X, which may be identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$) alkylamino(C$_1$–C$_4$)alkyl radical, a di[(C$_1$–C$_4$)alkyl] amino(C$_1$–C$_4$)alkyl radical (it being possible for the dialkyls to form a 5- or 6-membered carbon-based ring or heterocycle), a hydroxy(C$_1$–C$_4$)alkyl- or di[hydroxy (C$_1$–C$_4$)alkyl]amino(C$_1$–C$_4$)alkyl radical, an amino radical, a (C$_1$–C$_4$)alkyl- or di[(C$_1$–C$_4$)alkyl]amino radical; a halogen atom, a carboxylic acid group or a sulphonic acid group;

i is equal to 0, 1, 2 or 3;
p is equal to 0 or 1;
q is equal to 0 or 1;
n is equal to 0 or 1;
with the proviso that:
the sum p+q is other than 0;

when p+q is equal to 2, then n is equal to 0 and the groups $NR_{15}R_{16}$, and $NR_{17}R_{18}$ occupy the (2,3); (5,6); (6,7); (3,5) or (3,7) positions;

when p+q is equal to 1, then n is equal to 1 and the group $NR_{15}R_{16}$ (or $NR_{17}R_{18}$) and the OH group occupy the (2,3); (5,6); (6,7); (3,5) or (3,7) positions.

When the pyrazolo[1,5-a]pyrimidines of formula (IV) above are such that they contain a hydroxyl group on one of the positions 2, 5 or 7 α to a nitrogen atom, a tautomeric equilibrium exists represented, for example, by the following scheme:

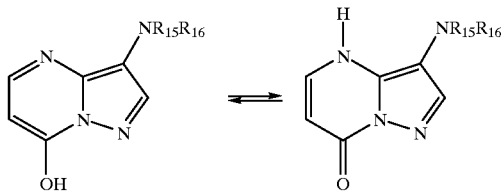

Among the pyrazolo[1,5-a]pyrimidines of formula (IV) above, mention may be made in particular of:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and the addition salts thereof and the tautomeric forms thereof, when a tautomeric equilibrium exists.

The pyrazolo[1,5-a]pyrimidines of formula (IV) above can be prepared by cyclization starting with an aminopyrazole, according to the syntheses described in the following references:

EP 628559 Beiersdorf-Lilly.
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
US 3907799 ICN Pharmaceuticals.

The pyrazolo[1,5-a]pyrimidines of formula (IV) above can also be prepared by cyclization starting from hydrazine, according to the syntheses described in the following references:

A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) in accordance with the invention preferably represent(s) from 0.0005 to 12% by weight approximately relative to the total weight of the ready-to-use dye composition, and even more preferably from 0.005 to 6% by weight approximately relative to this weight.

The choline oxidase used in the ready-to-use dye composition in accordance with the invention can be of animal, microbiological (bacterial, fungal or viral) or synthetic (obtained by chemical or biotechnological synthesis) origin.

As examples of sources of choline oxidase, mention may be made in particular of rat liver, bacteria such as Arthrobacter globiformis, Achromobacter cholinophagum or Alcaligenes, and fungi such as Cylindrocarpon didynum.

The choline oxidase used in the ready-to-use dye composition in accordance with the invention preferably represents from 0.01 to 20% by weight approximately relative to the total weight of the ready-to-use dye composition, and even more preferably from 0.1 to 5% by weight approximately relative to this weight.

According to the invention, the term "donor" refers to the different substrate(s) required for the functioning of the choline oxidase.

Among the donors for choline oxidase, mention may be made of choline and its addition salts with an acid, such as choline hydrochloride, and betaine aldehyde.

The donor(s) (or substrates) used in accordance with the invention preferably represent(s) from 0.01 to 20% by weight approximately relative to the total weight of the ready-to-use dye composition in accordance with the invention, and even more preferably from 0.1 to 5% approximately relative to this weight.

The ready-to-use dye composition in accordance with the invention can also contain one or more couplers and/or one or more direct dyes, in particular in order to modify the shades or to enrich them with glints.

Among the couplers which can be used in the ready-to-use dye compositions in accordance with the invention, mention may be made in particular of meta-phenylenediamines, meta-aminophenols, meta-diphenols and heterocyclic couplers such as, for example, indole derivatives, indoline derivatives, benzimidazole derivatives, benzomorpholine derivatives, sesamol derivatives and pyridine, pyrimidine and pyrazole derivatives, and the addition salts thereof with an acid.

These couplers can be chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or the support) for the ready-to-use dye composition in accordance with the invention generally consists of water or of a mixture of water and at least one organic solvent in order to dissolve the compounds which would not be sufficiently soluble in water. By way of organic solvent, mention may be made, for example, of $C_1$–$C_4$ alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the ready-to-use composition in accordance with the invention is chosen such that the enzymatic activity of the choline oxidase is sufficient. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (V) below:

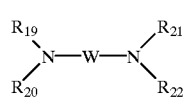

(V)

in which W is a propylene residue optionally substituted with a hydroxyl group or a $C_1$–$C_4$ alkyl radical; $R_{19}$, $R_{20}$, $R_{21}$ and $R_{22}$, which may be identical or different, represent a hydrogen atom or a $C_1$–$C_4$ alkyl or $C_{1-C4}$ hydroxyalkyl radical.

The ready-to-use dye composition in accordance with the invention can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the choline oxidase used in accordance with the invention, such as, for example, peroxidases, penetration agents, sequestering agents, fragrances, buffers, dispersing agents, conditioners such as, for example, volatile or non-volatile, modified or non-modified silicones, film-forming agents, ceramides, preserving agents and opacifiers.

Needless to say, a person skilled in the art will take care to select this or these optional complementary compound(s) such that the advantageous properties intrinsically associated with the ready-to-use dye composition in accordance with the invention are not, or are not substantially, adversely affected by the addition or additions envisaged.

The ready-to-use dye composition in accordance with the invention can be in various forms, such as in the form of liquids, creams or gels, which are optionally pressurized, or in any other form which is suitable for dyeing keratin fibres, and in particular human hair. In the case of a ready-to-use dye composition, the oxidation dyes(s) and the choline oxidase are present within the same ready-to-use composition, and consequently the said composition must be free of oxygen gas, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more precisely between 5 and 40 minutes.

According to one specific embodiment of the invention, the process includes a first step which consists in separately storing, on the one hand, a composition (A) comprising, in a medium which is suitable for dyeing, at least one oxidation base and, on the other hand, a composition (B) containing, in a medium which is suitable for dyeing, choline oxidase in the presence of at least one donor of the said choline oxidase, and then in mixing them together at the time of use, before applying this mixture to the keratin fibres.

Another subject of the invention is a multi-compartment dyeing device or "kit" or any other multi-compartment packaging system, a first compartment of which contains composition (A) as defined above and a second compartment of which contains composition (B) as defined above. These devices can be equipped with means for applying the desired mixture to the hair, such as the devices described in patent FR-2,586,913 in the name of the Applicant.

The examples which follow are intended to illustrate the invention without, however, limiting its scope.

EXAMPLES

Comparative Examples 1 and 2

The ready-to-use dye compositions below were prepared (contents in grams):

| COMPOSITION | 1 | 2(*) |
|---|---|---|
| para-Phenylenediamine (oxidation base) | 0.216 | 0.216 |
| 2,4-Diaminophenoxyethanol dihydrochloride (coupler) | 0.723 | 0.723 |
| Choline oxidase from Alcaligenes, at a concentration of 18 International Units (I.U.)/mg, sold by the company Sigma (enzyme in accordance with the invention) | 1.111 | — |
| Choline hydrochloride (donor in accordance with the invention) | 0.166 | — |
| Uricase from *Arthobacter globiformis*, at a concentration of 20 International Units (I.U.)/mg, sold by the company Sigma (enzyme not in accordance with the invention) | — | 1.0 |
| Uric acid (donor not in accordance with the invention) | — | 0.2 |
| Ethanol | 10.0 | 10.0 |
| Monoethanolamine qs | pH = 9.5 | pH = 9.5 |
| Demineralized water qs | 100 g | 100 g |

(*) Example not forming part of the invention

It is important to note that each of the ready-to-use dye compositions described above contain the same amount of enzyme, i.e. 20,000 I.U.

Each of the ready-to-use dye compositions described above was applied to locks of permed grey hair containing 90% white hairs, for 30 minutes. The hair was then rinsed, washed with a standard shampoo and then dried.

The colour of the locks was then evaluated, before and 24 hours after the dyeing operation, in the Munsell system using a Minolta CM 2002® calorimeter so as to determine the strength of the colorations obtained with each of the compositions described above.

The difference between the colour of a lock before dyeing and the colour of the lock after dyeing was calculated by applying the Nickerson formula $$\Delta E = 0.4 Co \Delta H + 6 \Delta V + 3 \Delta C$$

as described, for example, in "Couleur, Industrie et Technique": pages 14–17; vol No. 5; 1978.

In this formula, $\Delta E$ represents the colour difference between two locks, $\Delta H$, $\Delta V$ and $\Delta C$ represent the variation in absolute value of the parameters H, V and C, and Co represents the purity of the lock relative to which it is desired to evaluate the colour difference.

The strength of the coloration ($\Delta E$) is proportionately greater the higher the figure indicated.

The results are given in Table I below:

TABLE I

| EXAMPLE | Colour of the hair before dyeing | Colour of the hair after dyeing | Strength of the coloration | | | |
|---|---|---|---|---|---|---|
| | | | $\Delta H$ | $\Delta V$ | $\Delta C$ | $\Delta E$ |
| 1 | 4.2 Y 5.6/1.6 | 8.6 PB 2.6/2.4 | 45.6 | 3.0 | 0.8 | 49.6 |
| 2(*) | 4.2 Y 5.6/1.6 | 8.9 PB 2.9/1.6 | 45.3 | 2.7 | 0 | 45.2 |

(*): Example not forming part of the invention

These results show that the ready-to-use dye composition of Example 1 in accordance with the invention, i.e. the composition containing, as oxidizing system, the combination of choline oxidase and choline, leads to a coloration which is stronger than that obtained with the ready-to-use dye composition of Example 2 not forming part of the invention since it contains, as oxidizing system, the combination of uricase and uric acid. The use of the uricase/uric acid oxidizing system is described in particular in patent application EP-A-0,310,675.

What is claimed is:

1. A ready-to-use composition for the oxidation dyeing of keratin fibres wherein said composition comprises:
    at least one oxidation base,
    at least one choline oxidase, and
    at least one donor for said at least one choline oxidase.

2. The ready-to-use composition of claim 1 wherein said keratin fibers are human keratin fibers.

3. The ready-to-use composition of claim 2 wherein said human keratin fibers are hair.

4. The ready-to-use composition of claim 1, wherein said at least one oxidation base is chosen from para-phenylenediamines, double bases, para-aminophenols, ortho-aminophenols and heterocyclic oxidation bases.

5. The ready-to-use composition of claim 4, wherein said para-phenylenediamines are chosen from compounds of formula (I) and acid addition salts thereof:

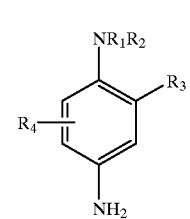

(I)

in which:
   $R_1$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals and $C_1$–$C_4$ alkyl radicals substituted with an entity chosen from nitrogenous groups, phenyl radicals and 4'-aminophenyl radicals;
   $R_2$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals and $C_1$–$C_4$ alkyl radicals substituted with a nitrogenous group;
   $R_3$ is chosen from a hydrogen atom, halogen atoms, $C_1$–$C_4$ alkyl radicals, $C_1$–$C_4$ monohydroxyalkyl radicals, $C_1-C_4$ hydroxyalkoxy radicals, acetylamino $(C_1-C_4)$alkoxy radicals, $C_1-C_4$ mesylaminoalkoxy radicals and carbamoylamino$(C_1-C_4)$alkoxy radicals;

$R_4$ is chosen from a hydrogen atom, halogen atoms and $C_1-C_4$ alkyl radicals.

6. The ready-to-use composition of claim 5, wherein said nitrogenous group(s) is (are) chosen from amino radicals, mono$(C_1-C_4)$alkylamino radicals, di$(C_1-C_4)$alkylamino radicals, tri$(C_1-C_4)$alkylamino radicals, monohydroxy $(C_1-C_4)$alkylamino radicals, imidazolinium radicals and ammonium radicals.

7. The ready-to-use composition of claim 5, wherein said halogen atoms are chosen from chlorine, bromine, iodine and fluorine atoms.

8. The ready-to-use composition of claim 4, wherein said para-phenylenediamines are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

9. The ready-to-use composition of claim 8, wherein said para-phenylenediamines are chosen from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and acid addition salts thereof.

10. The ready-to-use composition of claim 4, wherein said double bases are chosen from compounds corresponding to formula (II) and acid addition salts thereof:

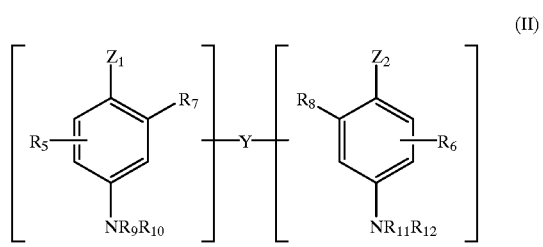

in which:

$Z_1$ and $Z_2$, which may be identical or different, are chosen from a hydroxyl radical, an —$NH_2$ radical which may be substituted with a substituent chosen from $C_1-C_4$ alkyl radicals and linker arms Y;

the linker arm Y is chosen from linear and branched alkylene chains containing from 1 to 14 carbon atoms, which may be interrupted by or terminated with at least one entity chosen from nitrogenous groups and hetero atoms, and optionally substituted with at least one substituent chosen from hydroxyl and $C_1-C_6$ alkoxy radicals;

$R_5$ and $R_6$ are chosen from a hydrogen atom, halogen atoms, $C_1-C_4$ alkyl radicals, $C_1-C_4$ monohydroxyalkyl radicals, $C_2-C_4$ polyhydroxyalkyl radicals, $C_1-C_4$ aminoalkyl radicals and linker arms Y;

$R_7$, $R_8$, $R_9$, $R_{10}$, $R_{11}$ and $R_{12}$, which may be identical or different, are chosen from a hydrogen atom, linker arms Y, and $C_1-C_4$ alkyl radicals;

it being understood that the compounds of formula (II) contain only one linker arm Y per molecule.

11. The ready-to-use composition of claim 10, wherein said heteroatoms are chosen from oxygen, sulphur and nitrogen atoms.

12. The ready-to-use composition of claim 10, wherein said nitrogenous groups are chosen from amino radicals, mono$(C_1-C_4)$alkylamino radicals, di$(C_1-C_4)$alkylamino radicals, tri$(C_1-C_4)$alkylamino radicals, monohydroxy $(C_1-C_4)$alkylamino radicals, imidazolinium radicals and ammonium radicals.

13. The ready-to-use composition of claim 4, wherein said double bases are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and acid addition salts thereof.

14. The ready-to-use composition of claim 13, wherein said double bases are chosen from N,N'-bis(β-hydroxyethyl)-N,N'-bis(4'-aminophenyl)-1,3-diaminopropanol, 1,8-bis(2,5-diaminophenoxy)-3,5-dioxaoctane, and acid addition salts thereof.

15. The ready-to-use composition of claim 4, wherein said para-aminophenols are chosen from compounds corresponding to formula (III) and acid addition salts thereof:

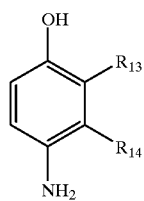

(III)

in which:
R$_{13}$ is chosen from a hydrogen atom, halogen atoms, C$_1$–C$_4$ alkyl radicals, C$_1$–C$_4$ monohydroxyalkyl radicals, (C$_1$–C$_4$)alkoxy(C$_1$–C$_4$)alkyl radicals, C$_1$–C$_4$ aminoalkyl radicals and hydroxy(C$_1$–C$_4$)alkylamino (C$_1$–C$_4$)alkyl radicals, R$_{14}$ is chosen from a hydrogen atom, halogen atoms, C$_1$–C$_4$ alkyl radicals, C$_1$–C$_4$ monohydroxyalkyl radicals, C$_2$–C$_4$ polyhydroxyalkyl radicals, C$_1$–C$_4$ aminoalkyl radicals, C$_1$–C$_4$ cyanoalkyl radicals and (C$_1$–C$_4$)alkoxy-(C$_1$–C$_4$)alkyl radicals, it being understood that at least one of the radicals R$_{13}$ or R$_{14}$ represents a hydrogen atom.

16. The ready-to-use composition of claim 4, wherein said para-aminophenols are chosen from para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)-phenol, 4-amino-2-((β-hydroxyethyl)aminomethyl)phenol, 4-amino-2-fluorophenol and acid addition salts thereof.

17. The ready-to-use composition of claim 4, wherein said ortho-aminophenols are chosen from 2-aminophenol, 2-amino-5-methylphenol, 2-amino-6-methylphenol, 5-acetamido-2-aminophenol and acid addition salts thereof.

18. The ready-to-use composition of claim 4, wherein said heterocyclic bases are chosen from pyridines, pyrimidines, pyrazoles, pyrazolopyrimidines and acid addition salts thereof.

19. The ready-to-use composition of claim 18, wherein said pyrazolopyrimidines are chosen from compounds of formula (IV), acid addition salts thereof, base addition salts thereof, and tautomeric forms thereof, when there exists a tautomeric equilibrium:

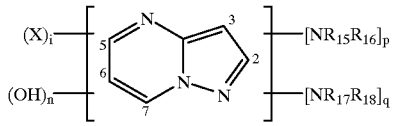

(IV)

in which:
R$_{15}$, R$_{16}$, R$_{17}$ and R$_{18}$, which are identical or different, are chosen from a hydrogen atom, C$_1$–C$_4$ alkyl radicals, aryl radicals, C$_1$–C$_4$ hydroxyalkyl radicals, C$_2$–C$_4$ polyhydroxyalkyl radicals, (C$_1$–C$_4$)alkoxy(C$_1$–C$_4$) alkyl radicals, C$_1$–C$_4$ aminoalkyl radicals wherein the amine may be protected by an acetyl, ureido or sulphonyl radical, (C$_1$–C$_4$)alkylamino(C$_1$–C$_4$)alkyl radicals, di((C$_1$–C$_4$)alkyl)amino(C$_1$–C$_4$)alkyl radicals wherein the dialkyl radicals may form a ring chosen from 5- and 6- membered carbon-based and heterocyclic rings, hydroxy(C$_1$–C$_4$)alkylamino(C$_1$–C$_4$)alkyl radicals, and di(hydroxy(C$_1$–C$_4$)alkyl)amino(C$_1$–C$_4$) alkyl radicals;

the X radicals, which are identical or different, are chosen from a hydrogen atom, C$_1$–C$_4$ alkyl radicals, aryl radicals, C$_1$–C$_4$ hydroxyalkyl radicals, C$_2$–C$_4$ polyhydroxyalkyl radicals, C$_1$–C$_4$ aminoalkyl radicals, (C$_1$–C$_4$)alkylamino(C$_1$–C$_4$)alkyl radicals, di((C$_1$–C$_4$) alkyl)amino(C$_1$–C$_4$)alkyl radicals wherein the dialkyls may form a ring chosen from 5- and 6-membered carbon-based and heterocyclic rings, hydroxy(C$_1$–C$_4$) alkylamino(C$_1$–C$_4$)alkyl radicals, di(hydroxy(C$_1$–C$_4$) alkyl)-amino(C$_1$–C$_4$)alkyl radicals, amino radicals, (C$_1$–C$_4$)alkylamino radicals, di((C$_1$–C$_4$)alkyl)amino radicals, halogen atoms, carboxylic acid groups and sulphonic acid groups;

i has the value 0, 1, 2 or 3;
p has the value 0 or 1;
q has the value 0 or 1;
n has the value 0 or 1;
with the proviso that:
the sum p+q is other than 0;
when p+q is equal to 2, then n has the value 0 and the NR$_{15}$R$_{16}$ and NR$_{17}$R$_{18}$ groups occupy the (2,3), (5,6), (6,7), (3,5) or (3,7) positions;
when p+q is equal to 1, then n has the value 1 and the NR$_{15}$R$_{16}$ or NR$_{17}$R$_{18}$ group and the OH group occupy the (2,3), (5,6), (6,7), (3,5) or (3,7) positions.

20. The ready-to-use composition of claim 19, wherein said compounds of formula (IV) are chosen from
pyrazolo(1,5-a)pyrimidine-3,7-diamine;
2,5-dimethylpyrazolo(1,5-a)pyrimidine-3,7-diamine;
pyrazolo(1,5-a)pyrimidine-3,5-diamine;
2,7-dimethylpyrazolo(1,5-a)pyrimidine-3,5-diamine;
3-aminopyrazolo(1,5-a)pyrimidin-7-ol;
3-aminopyrazolo(1,5-a)pyrimidin-5-ol;
2-(3-aminopyrazolo(1,5-a)pyrimidin-7-ylamino)ethanol;
2-(7-aminopyrazolo(1,5-a)pyrimidin-3-ylamino)ethanol;
2-((3-aminopyrazolo(1,5-a)pyrimidin-7-yl)-(2-hydroxyethyl)amino)ethanol;
2-((7-aminopyrazolo(1,5-a)pyrimidin-3-yl)-(2-hydroxyethyl)amino)ethanol;
5,6-dimethylpyrazolo(1,5-a)pyrimidine-3,7-diamine;
2,6-dimethylpyrazolo(1,5-a)pyrimidine-3,7-diamine;
2,5,N7,N7-tetramethylpyrazolo(1,5-a)pyrimidine-3,7-diamine;
acid addition salts thereof, base addition salts thereof, and tautomeric forms thereof, when there exists a tautomeric equilibrium.

21. The ready-to-use composition of claim 1, wherein said at least one oxidation base is present in an amount ranging from 0.0005 to 12% by weight relative to the total weight of the composition.

22. The ready-to-use composition of claim 21, wherein said at least one oxidation base is present in an amount ranging from 0.005 to 6% by weight relative to the total weight of the composition.

23. The ready-to-use composition of claim 1, wherein said at least one choline oxidase is chosen from those of animal, microbiological, and synthetic origin.

24. The ready-to-use composition of claim 1, wherein said at least one choline oxidase is present in an amount ranging from 0.01 to 20% by weight relative to the total weight of the composition.

25. The ready-to-use composition of claim 24, wherein said at least one choline oxidase is present in an amount ranging from 0.1 to 5% by weight relative to the total weight of the composition.

26. The ready-to-use composition of claim 1, wherein said at least one donor is chosen from choline, acid addition salts of choline, and betaine aldehyde.

27. The ready-to-use composition of claim 1, wherein said at least one donor is present in an amount ranging from 0.01 to 20% by weight relative to the total weight of the composition.

28. The ready-to-use composition of claim 27, wherein said at least one donor is present in an amount ranging from 0.1 to 5% by weight relative to the total weight of the composition.

29. The ready-to-use composition of claim 1, wherein said composition further comprises at least one additional ingredient chosen from couplers and direct dyes.

30. The ready-to-use composition of claim 29, wherein said couplers are chosen from meta-phenylenediamines, meta-aminophenols, meta-diphenols, heterocyclic couplers and the acid addition salts thereof.

31. The ready-to-use composition of claim 29, wherein said couplers are chosen from indoles, indolines, benzimidazoles, benzomorpholines, sesamols, pyridines, pyrimidines, and pyrazoles, and the acid addition salts thereof.

32. The ready-to-use composition of claim 29, wherein said couplers are chosen from 2-methyl-5-aminophenol, 5-N-($\beta$-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-($\beta$-hydroxyethyloxy)benzene, 2-amino-4-($\beta$-hydroxyethylamino)-1-methoxybenzene, 1,3-diaminobenzene, 1,3-bis(2,4-diaminophenoxy)propane, sesamol, $\alpha$-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and the acid addition salts thereof.

33. The ready-to-use composition of claim 29, wherein said couplers are present in an amount ranging from 0.0001 to 10% by weight relative to the total weight of the composition.

34. The ready-to-use composition of claim 33, wherein said couplers are present in an amount ranging from 0.005 to 5% by weight relative to the total weight of the composition.

35. The ready-to-use composition of claim 1, wherein said composition further comprises a medium suitable for dyeing, said medium comprising water or a mixture of water and at least one organic solvent.

36. The ready-to-use composition of claim 35, wherein said at least one organic solvent is chosen from $C_1$–$C_4$ alkanols, glycerol, glycols, glycol ethers and aromatic alcohols.

37. The ready-to-use composition of claim 35, wherein said at least one organic solvent is present in an amount ranging from 1 to 40% by weight relative to the total weight of the composition.

38. The ready-to-use composition of claim 37, wherein said at least one organic solvent is present in an amount ranging from 5 to 30% relative to the total weight of the composition.

39. The ready-to-use composition of claim 1, wherein said composition has a pH ranging from 5 to 11.

40. The ready-to-use composition of claim 39, wherein said pH ranges from 6.5 to 10.

41. The ready-to-use composition of claim 1, wherein said composition is in the form of a liquid, a cream, a gel or any other form appropriate for dyeing keratin fibers.

42. The ready-to-use composition of claim 1, wherein said at least one oxidation base and said at least one choline oxidase are present within the same ready-to-use composition and said composition is free of oxygen gas.

43. A method for dyeing keratin fibres, comprising the steps of contacting said fibres for a time sufficient to achieve color development, with a ready-to-use dye composition comprising:

at least one oxidation base, at least one choline oxidase, and at least one donor for said at least one choline oxidase.

44. The method of claim 43, wherein said keratin fibers are human keratin fibers.

45. The method of claim 44, wherein said human keratin fibers are hair.

46. The method of claim 43, wherein said time sufficient ranges from 3 to 60 minutes.

47. The method of claim 46, wherein said time sufficient ranges from 5 to 40 minutes.

48. A method for dyeing keratin fibres, comprising separately storing a first composition comprising at least one oxidation base and a second composition containing at least one choline oxidase in the presence of at least one donor of said at least one choline oxidase, and thereafter mixing said first composition with said second composition and applying this mixture to the keratin fibres.

49. A multi-compartment dyeing device or kit for dyeing keratin fibers, comprising at least two separate compartments, wherein a first compartment contains a composition comprising at least one oxidation base and a second compartment contains a composition comprising at least one choline oxidase in the presence of at least one donor of said choline oxidase.

* * * * *